United States Patent
Palushi et al.

(10) Patent No.: US 12,350,033 B2
(45) Date of Patent: Jul. 8, 2025

(54) DEVICE AND METHOD TO DETECT AND REMOVE BLOOD CLOTS FOR TREATMENT OF ISCHEMIC STROKE USING FORCE AND ELECTROMAGNETIC SENSING

(71) Applicants: DePuy Synthes Products, Inc., Raynham, MA (US); BIOSENSE WEBSTER (ISRAEL) LTD., Yokneam (IL)

(72) Inventors: Jetmir Palushi, Raynham, MA (US); Fatemeh Akbarian, Yokneam (IL)

(73) Assignees: DEPUY SYNTHES PRODUCTS, INC., Raynham, MA (US); BIOSENSE WEBSTER (ISRAEL) LTD., Yokneam (IL)

( * ) Notice: Subject to any disclaimer, the term of this patent is extended or adjusted under 35 U.S.C. 154(b) by 253 days.

(21) Appl. No.: 18/096,622

(22) Filed: Jan. 13, 2023

(65) Prior Publication Data
US 2023/0165483 A1   Jun. 1, 2023

Related U.S. Application Data

(62) Division of application No. 16/001,427, filed on Jun. 6, 2018, now Pat. No. 11,839,460.

(51) Int. Cl.
*A61B 5/00* (2006.01)
*A61B 5/06* (2006.01)
(Continued)

(52) U.S. Cl.
CPC ............ *A61B 5/062* (2013.01); *A61B 5/0048* (2013.01); *A61B 5/0057* (2013.01); *A61B 5/065* (2013.01);
(Continued)

(58) Field of Classification Search
CPC ..... A61B 34/20; A61B 5/0048; A61B 5/0057; A61B 5/065; A61B 17/221;
(Continued)

(56) References Cited

U.S. PATENT DOCUMENTS 6,511,492 B1 * 1/2003 Rosenbluth ...... A61B 17/22032
606/159
8,585,732 B2  11/2013 Tomlin
(Continued)

FOREIGN PATENT DOCUMENTS

CN     1308508 A    8/2001
CN   103505181 A    1/2014
(Continued)

OTHER PUBLICATIONS

Partial Search Report dated Oct. 1, 2019, issued in corresponding European Application No. 19178388.5.
(Continued)

*Primary Examiner* — Jeffrey G Hoekstra
*Assistant Examiner* — Adam D. Kolkin
(74) *Attorney, Agent, or Firm* — TROUTMAN PEPPER LOCKE LLP (57) ABSTRACT

A device can detect and retrieve a blood clot by advancing a catheter with a clot sensing element through a patient's vascular system. The catheter can map, using an electromagnetic sensor disposed at a distal end of the clot sensing element, the patient's vascular system. A force sensor can generate a position signal indicating the clot sensing element contacted the clot in the patient's vascular system. Once located, a blood clot retrieval device can be deployed through the catheter and a lumen in the clot sensing element to remove the clot from the patient's vascular system.

13 Claims, 6 Drawing Sheets

(51) Int. Cl.
    *A61B 17/221* (2006.01)
    *A61B 34/20* (2016.01)
    *A61F 2/01* (2006.01)
    *A61B 17/22* (2006.01)
    *A61M 25/01* (2006.01)

(52) U.S. Cl.
    CPC ............ *A61B 17/221* (2013.01); *A61B 34/20* (2016.02); *A61F 2/012* (2020.05); *A61B 2017/22094* (2013.01); *A61B 2017/2215* (2013.01); *A61B 2034/2051* (2016.02); *A61M 25/0127* (2013.01)

(58) Field of Classification Search
    CPC .. A61B 2034/2051; A61B 2017/22094; A61B 2017/2215; A61F 2/01; A61M 25/0127
    See application file for complete search history.

(56) References Cited

U.S. PATENT DOCUMENTS

| | | |
|---|---|---|
| 2002/0198492 A1 | 12/2002 | Miller et al. |
| 2006/0106375 A1 | 5/2006 | Werneth et al. |
| 2008/0009772 A1 | 1/2008 | Tyler et al. |
| 2013/0317425 A1 | 11/2013 | Angel et al. |
| 2014/0058407 A1 | 2/2014 | Tsekos et al. |
| 2016/0276739 A1* | 9/2016 | Buesseler ................ A61B 5/06 |

FOREIGN PATENT DOCUMENTS

| | | |
|---|---|---|
| EP | 2449996 A1 | 5/2012 |
| EP | 2679149 A1 | 1/2014 |
| IN | 102551876 A | 7/2012 |

OTHER PUBLICATIONS

Search Report issued in Chinese Patent Application No. 201910491653.7 dated May 12, 2022, English translation only.

* cited by examiner

DEVICE AND METHOD TO DETECT AND REMOVE BLOOD CLOTS FOR TREATMENT OF ISCHEMIC STROKE USING FORCE AND ELECTROMAGNETIC SENSING

CROSS REFERENCE TO RELATED APPLICATION

The present application is a divisional application of U.S. patent application Ser. No. 16/001,427 filed Jun. 6, 2018. The entire contents of which are hereby incorporated by reference.

FIELD OF INVENTION

The invention relates to a force sensing and fast anatomical mapping sensor package and a novel clot capture device.

BACKGROUND

Ischemic stroke is the most prevalent (~75%) of the two types of strokes. The other type of stroke being hemorrhagic stroke, which deals with treatment of aneurysms. Ischemic stroke occurs when the blood vessels that supply the blood to the brain are clotted from plaque buildup within a vessel lumen. This results in blood supply interruption to the brain, resulting in ischemic stroke because of the blood clot.

Current devices are advanced to the blood clotting area through the aid of a guidewire. The guidewire is placed within the clot region by feel feedback. One the surgeon believes she is in the clot region, she advances the catheter and the clot retrieving device. The force feedback is not accurate all the time due to the clot being located far away from the point of guidewire introduction. In addition, the advancement of the guidewire can be progressed in a false passage and the surgeon has to retry a different passage again, until resistance is felt from the guidewire.

Additionally, the current imaging techniques use fluoroscopic radiation to track the movement of the guidewire/catheter. Fluoroscopy involves passing a continuous X-ray beam through the body part to be imaged and sent to a video monitor so that the body part and the motion of the guidewire/catheter can be seen in detail. The use of fluoroscopy is associated with radiation-related risks, including radiation-induced injuries to the skin and underlying tissues ("burns"), which occur shortly after the exposure, and radiation-induced cancers.

Thus, what is needed is a device that can reach a clot region with high accuracy and avoid the harmful use of radiation.

SUMMARY

Examples of the present invention can include a force sensing element with center lumen. An example device can have a catheter with an inner lumen, a distal end, and the sensing element disposed at the distal end. An electromagnetic transceiver can emit or receive a signal and is fixed to a proximal end of the sensing element. An electromagnetic sensor can receive the signal and is disposed at the distal end of the sensing element. The sensor can be slidable along the sensing element and generate a position signal. A spring can be disposed between the transceiver and the sensor providing resistance to a proximal movement of the sensor. When the sensor is in a first position, the signal received by the sensor can have a first frequency and a first power and when the sensor is in a second position, the signal received by the sensor can have a second frequency and a second power. Also, the position signal is generated based on at least one of the first frequency, the second frequency, the first power, and the second power. The force sensing element can also have a fast anatomical mapping sensor.

The force sensing element above also can have the first position being a fully distal position on the sensing element, and the second position being a proximal position near the transceiver. A spring constant can control an amount of force needed to move the sensor.

An electromagnetic sensing element with a center lumen may include a hollow tube with a proximal end, a distal end, and an inner lumen. A coil can be wound around the tube, disposed outside the inner lumen, and provide a mapping signal. A wire can be connected to the coil and can transmit the mapping signal to a processor, and the center lumen has an inner diameter configured to pass a neurovascular device. The tube can be a hollow rigid ferrite tube approximately a length of the electromagnetic sensing element; and the wire can be a twisted pair.

An example of a device to remove an obstruction in a vascular system may include a delivery tube and capture anchors disposed in the delivery tube with an advancing position and a capture position. When the capture anchors are in the advancing position they are approximately parallel to a center axis of the delivery tube, and in the capture position, a distal end of each of the plurality of capture anchors expand outwards and curves proximally. In examples, the obstruction is captured within the curve of each of the plurality of capture anchors. Further, the capture anchors can expand circumferentially.

A method of detecting and retrieving a blood clot can include the steps of advancing a catheter with a clot sensing element through a patient's vascular system. The catheter can map, using an electromagnetic sensor disposed at a distal end of the clot sensing element, the patient's vascular system. The force sensor can generate a position signal, indicating the clot sensing element contacted the clot in the patient's vascular system. Once located, a blood clot retrieval device can be deployed through the catheter and a lumen in the clot sensing element to remove the clot from the patient's vascular system.

The deploying step further can include penetrating through the clot using a plurality of capture anchors in an advancing position, expanding the plurality of capture anchors into a capture position; and withdrawing the blood clot retrieval device back into the catheter with a portion of the blood clot. Withdrawing can further include aspirating through the catheter.

The generating step can include disposing an electromagnetic transceiver at a proximal end of the clot sensing element and disposing an electromagnetic sensor at the distal end of the clot sensing element a first distance from the transceiver. A spring can be disposed between the transceiver and the sensor, the spring providing resistance to a proximal movement of the sensor. A signal can be emitted from the transceiver and received at the sensor. The proximal movement of the sensor can be determined based on at least one of a change in frequency of the signal and a change in power of the signal. The position signal can be generated based on the proximal movement of the sensor.

The receiving step can include receiving at the sensor the signal comprising a first frequency and a first power when the sensor is at the first distance and receiving at the sensor the signal comprising a second frequency and a second power when the sensor is at a second distance shorter than the first distance. The change from the first frequency to the second frequency can be based on the change from the first distance to the second distance, and the change from the first power to the second power is based on the change from the first distance to the second distance.

The mapping step can dispose a hollow tube with a proximal end, and distal end, and an inner lumen. A coil can be wound around the tube, disposed outside the inner lumen, and provides a mapping signal. A wire can be connected to the coil and can transmit the mapping signal to a processor and the inner lumen has an inner diameter configured to pass a neurovascular device. The hollow tube can have a hollow rigid ferrite tube approximately a length of the electromagnetic sensing element and the wire can be a twisted pair.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Figures 1, 2A:
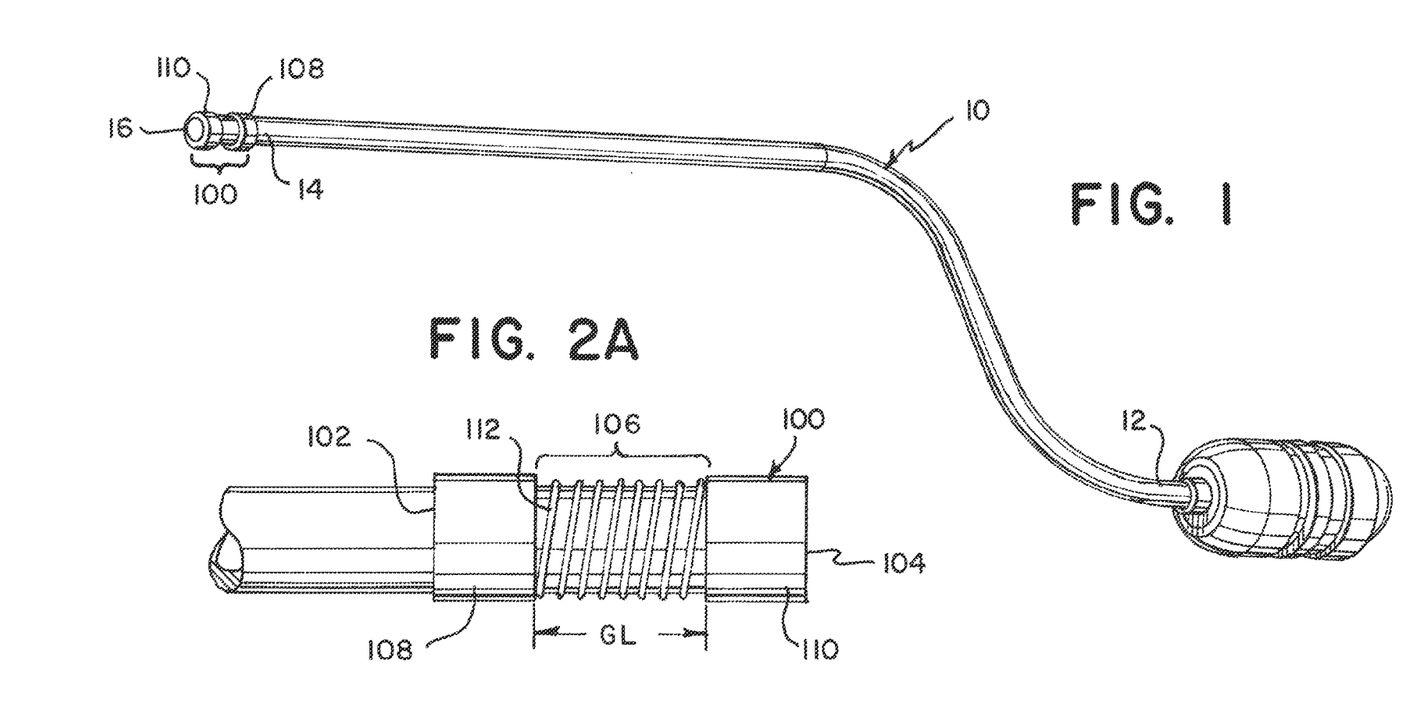
FIG. 1 is a front side perspective view of the sensing element disposed on a catheter and advancer.
FIG. 2A is a side view of the force sensing element in the uncontracted position.
Figure 2B:
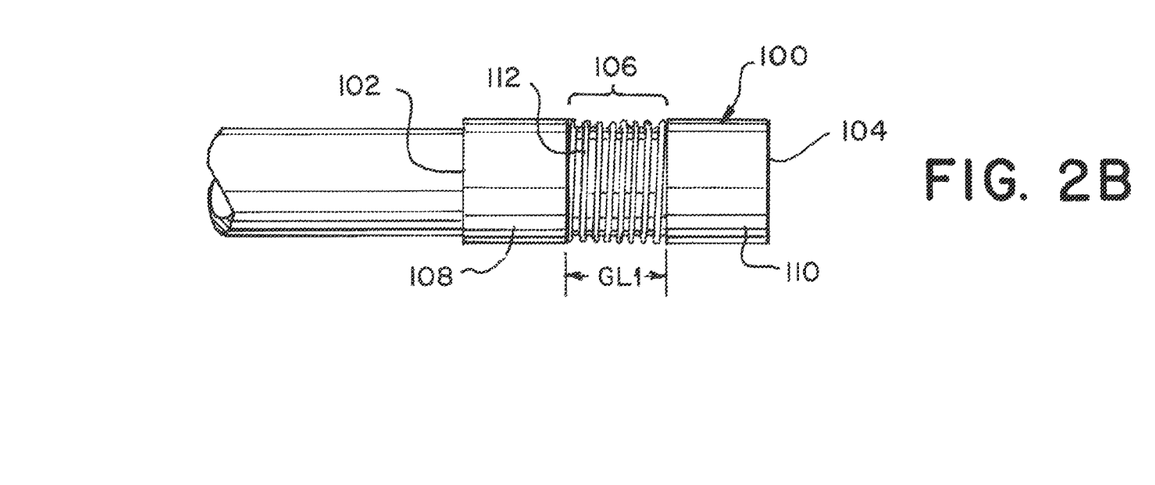
FIG. 2B is a side view of the force sensing element in the contracted position, typically in contact with an obstruction.

FIGS. 1, 2A, and 2B illustrate an obstruction sensing element 100 using force detection, with a center lumen 16. FIG. 1 illustrates a catheter 10 having a proximal end 12, a distal end 14 and the inner lumen 16. At the proximal end 12 can be a handle to steer the catheter 10, certain electronics in support of the invention and an advancer for the obstruction capturing device 300. At the distal end 14 of the catheter 10 can be disposed a force sensing element 100.

The force sensing element 100 can include a proximal end 102, a distal end 104, and a gap 106 therebetween. An electromagnetic transceiver 108 can be fixed to the proximal end 102 of the force sensing element 100. An electromagnetic sensor 110 can be disposed at the distal end 104 of the force sensing element 100 and separated from the transceiver 108 by the gap 106. The electromagnetic sensor 110 is also slidable along the force sensing element 100. A spring 112 is disposed between the electromagnetic transceiver 108 and the electromagnetic sensor 110 and provides resistance to a proximal movement of the electromagnetic sensor 110.

The obstruction sensing element 100 acts as a force sensing element to determine if the tip of the catheter 10 contacts an obstruction C in the vasculature V (see FIGS. 3A and 3B and 8A and 8B). The obstruction C is typically a blood clot, but the sensor can be used to sense the impact into any obstruction, including a previously deployed stent or other natural or implanted features. To determine contact with the obstruction C, the transceiver 108 can transmit a signal 114 and that signal is received by the electromagnetic sensor 110. The electromagnetic sensor 110 is displaceable along the catheter 10 and the spring 112 applies a distally directed force. When the electromagnetic sensor 110 contacts the obstruction C, it is pushed proximally, closing the gap 106 between the electromagnetic sensor 110 and the electromagnetic transceiver 108. Said differently, in the uncontacted condition, the gap 106 has an at rest gap length GL and then once in contact, the gap 106 shrinks so the distance between the electromagnetic sensor 110 and the transceiver 108 is now a contact gap length GL1. The contact gap length GL1 is always smaller than the at rest gap length GL (i.e., GL>GL1). This change in distance changes the nature of the received signal and provides a position signal.

The electromagnetic sensor 110 can detect whether the signal being received from the transceiver 108 has a frequency of frequency F1 or frequency F2 or frequency Fn. The electromagnetic transceiver 108 can then know the relative location of the electromagnetic sensor 110 relative to the electromagnetic transceiver 108 since the electromagnetic transceiver 108 is emitting signals, in one example, with a fixed initial frequency and/or wavelength. The electromagnetic sensor 110 can be a coil that can receive/transmit the signal. In one example, the electromagnetic sensor 110 can be a passive coil that charges and discharges based on the signal received.

The emitted signal from the electromagnetic transceiver 108 can have a frequency to detect spring 112 compression. The spring compression can be tuned with a spring constant (k) in a way that it can have enough distance changes based on blood clot C variations. When a blood clot C is hits the spring 112, the spring compresses, resulting in a smaller distance than when the catheter 10 has not hit a blood clot. This compression can result in the signal from the electromagnetic transceiver 108 to the electromagnetic sensor 110 traveling faster and the signal can have a higher strength. Thus, the electromagnetic sensor 110 can detect whether the distal end 14 of the catheter 10 has encountered an obstruction C. See, FIGS. 3A & 3B.

Figures 3A, 3B:
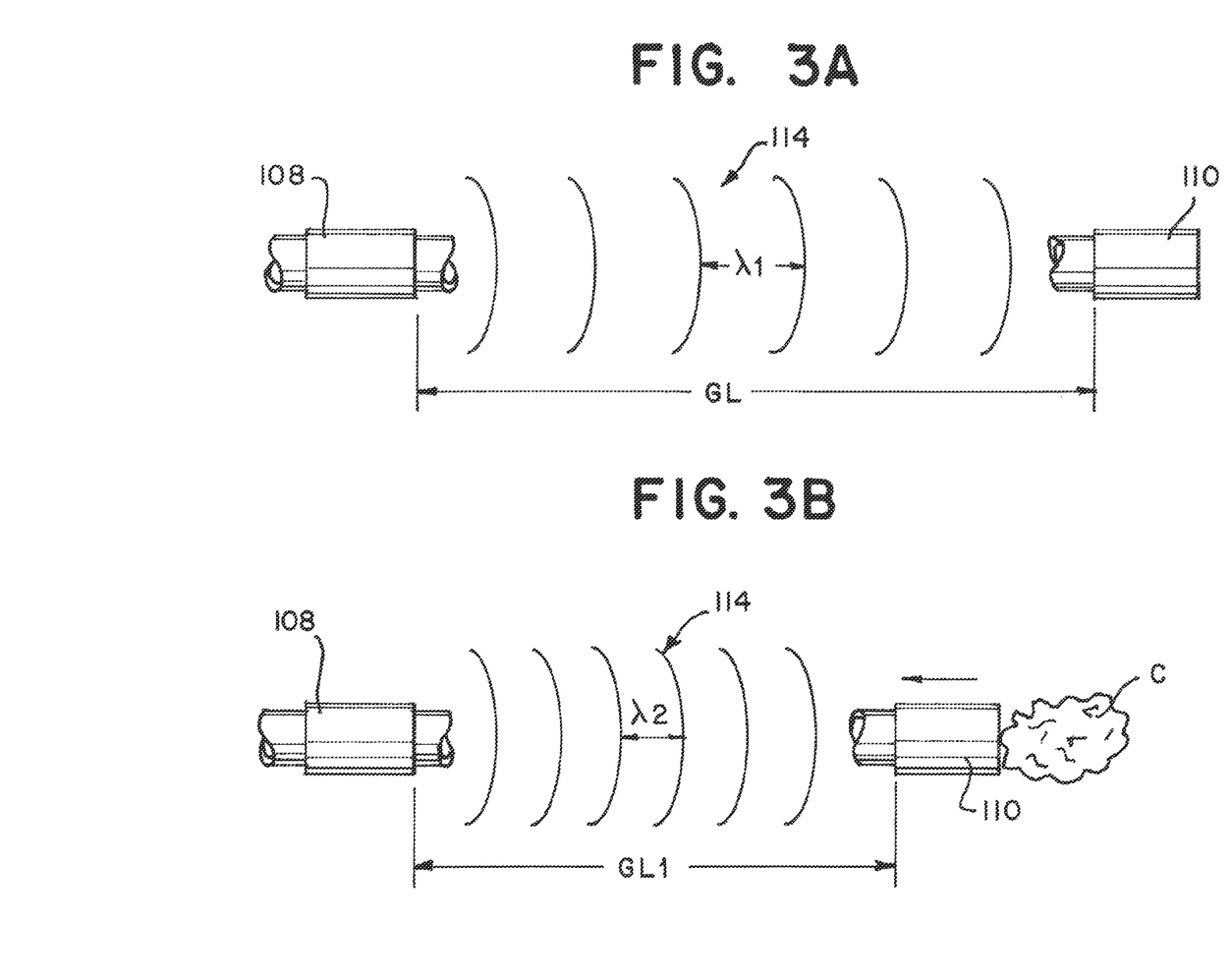
FIG. 3A is a view of the transmitter and sensor with signals at the at rest position.
FIG. 3B is a view of the transmitter and sensor with signals at the at contact position.

Alternately, when the electromagnetic sensor 110 is in a first position, i.e., uncontacted, the signal 114 received by the sensor 110 comprises a first frequency F1, and wavelength λ1, and a first power P1, as illustrated in FIG. 3A. The electromagnetic transceiver 108 and electromagnetic sensor 110 are at the at rest position with full gap length GL. As the electromagnetic sensor 110 contacts the obstruction C, it moves to a second position (obstruction contact), the signal 114 received by the electromagnetic sensor 110 now has a second frequency F2, due to a second wavelength λ2 and a second power P2, as illustrated in FIG. 3B.

One of ordinary skill is aware that frequency and wavelength are related through the speed of light (c), $F=c/\lambda$. The perceived change in frequency/wavelength identified by the electromagnetic sensor 110 during movement can be a product of the doppler effect. Knowing the emission frequency F1 and the second frequency F2, the distance the electromagnetic sensor 110 has moved can be calculated. In addition, knowing the spring constant (k) of the spring 112, allows one to calculate how much force was needed to move the sensor 110 the detected distance. The force required can then be used to determine the general nature of the obstruction C. The difference in transmitted and received signal power P1, P2 can also be calibrated to determine distance the electromagnetic sensor 110 moved. As the electromagnetic sensor 110 moves closer to the electromagnetic transceiver 108, the power increases. Thus, a position signal can be generated based on the first frequency F1, the second frequency F2, the first power P1, and/or the second power P2. The force sensing element 100 can also include a fast anatomical mapping (FAM) sensor, as described below.

Figures 4, 5, 6, 7:
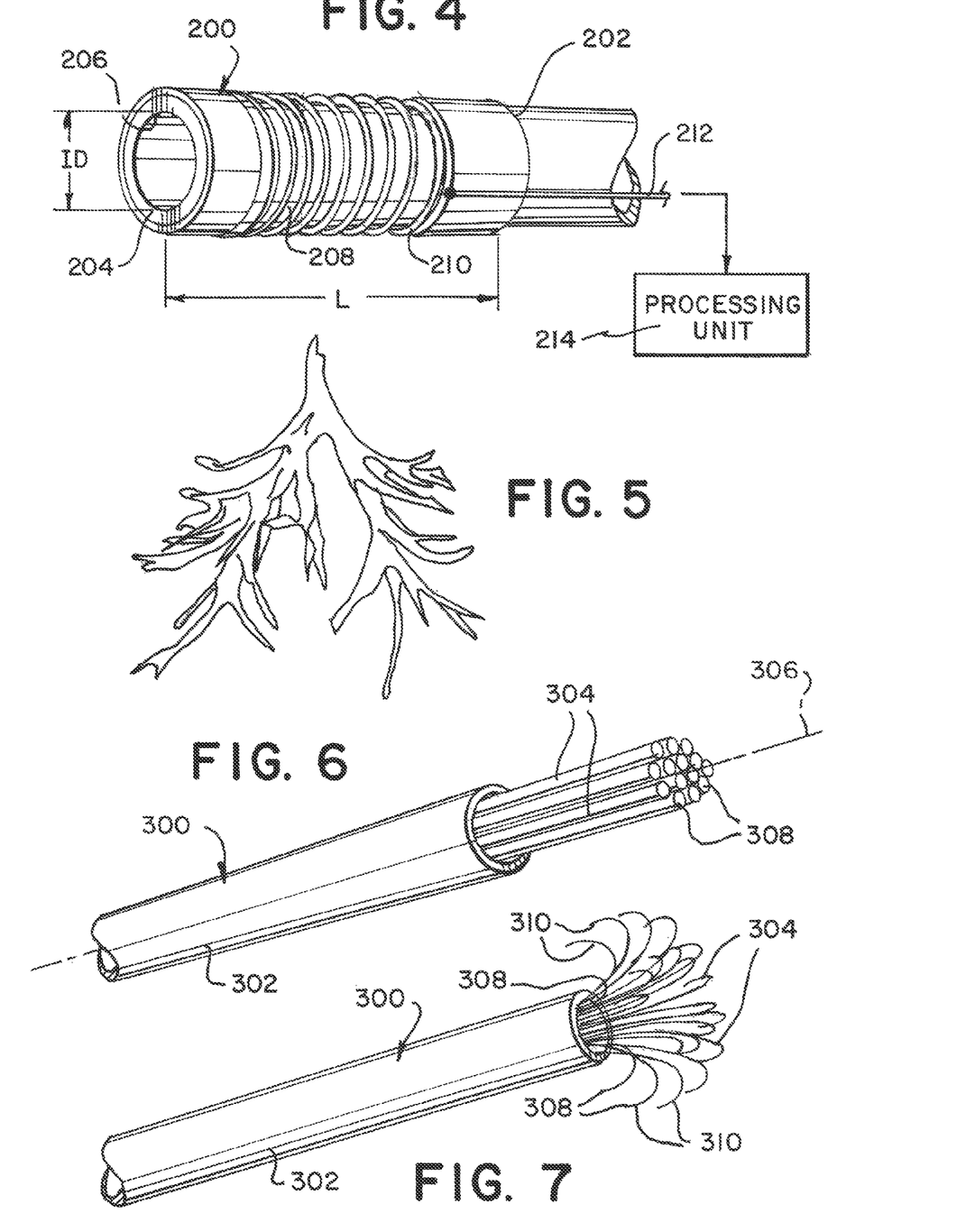
FIG. 4 is a front-side perspective view of the sensing element.
FIG. 5 is an example of a 3D image created by Fast Anatomical Mapping (FAM) branches of the lung.
FIG. 6 is a front-side perspective view of an obstruction capture device of the present invention in the advancing position.
FIG. 7 is a front-side perspective view of an obstruction capture device of the present invention in the capture position.

FIGS. 4 and 5 illustrate an additional example of a fast anatomical mapping (FAM) sensor or an electromagnetic sensing element 200 with a center lumen 206. The electromagnetic sensing element 200 has a proximal end 202, distal end 204, and the lumen 206 therethrough. The inner lumen 206 has an inner diameter (ID) configured to pass a neurovascular device. The electromagnetic sensing element 200 can have a hollow tube 208 spanning from the proximal end 202, and distal end 204 and shares the inner lumen 206. A coil 210 can be wound around the tube 208, disposed outside the inner lumen 206, and can provide a mapping signal. A wire 212 can be connected to the coil 210 and transmit the mapping signal to a processing unit 214. Typical FAM sensors do not have an inner lumen 206 to pass neurovascular devices. This adds an extra step to the surgical process since the mapping must be done first and then the neurovascular device can be introduced. In the present invention, the neurovascular device can be introduced as the mapping is being performed. Thus, a clot retrieving device can be introduced and used without compromising the accuracy of the location of the electromagnetic sensing element 200.

An example of the electromagnetic sensing element 200 can be a coil like inductor that is constructed as follows. A very thin layer hollow rigid ferrite tube 208 can be approximately a length L of the electromagnetic sensing element 200 and the inner diameter ID can be the same as the inner diameter of a catheter sheath (not illustrated). A wire (coil) 210 can be wound onto the thin layer ferrite tube 208. A sensor wire 212, in one example a thin twisted pair wire, can be attached via solder onto the winded coil 210 that acts as the sensor that carries a mapping signal from the sensor coil to a processing unit 214. The electromagnetic sensing element's 200 open inner diameter ID/lumen 206 allows for neurovascular instruments to pass through.

Disposing the electromagnetic sensing element 200 at the distal end 204 of the device allows the surgeon to know exactly where the catheter is in the vascular system as she tries to locate the obstruction/blood clot C. This is done by plotting a 3D image as the catheter 10 is advanced. FIG. 5 illustrates the plotting of lung airway branches, which are very similar to blood vessel branches. One of the advantages is that if the catheter is advanced in a direction where the 3D image is constructed, and no blood clot is found, the surgeon does not have to pursue the same passage again.

Figure 8A:
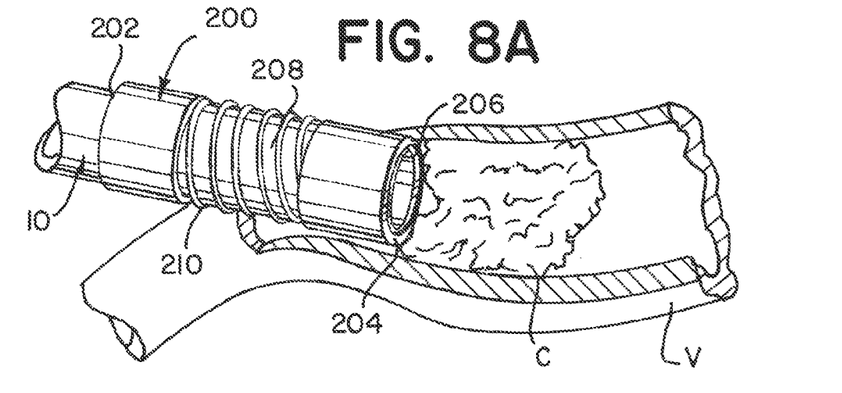
FIG. 8A illustrates an obstruction sensing and capture device in the vasculature encountering an obstruction.
Figure 8B:
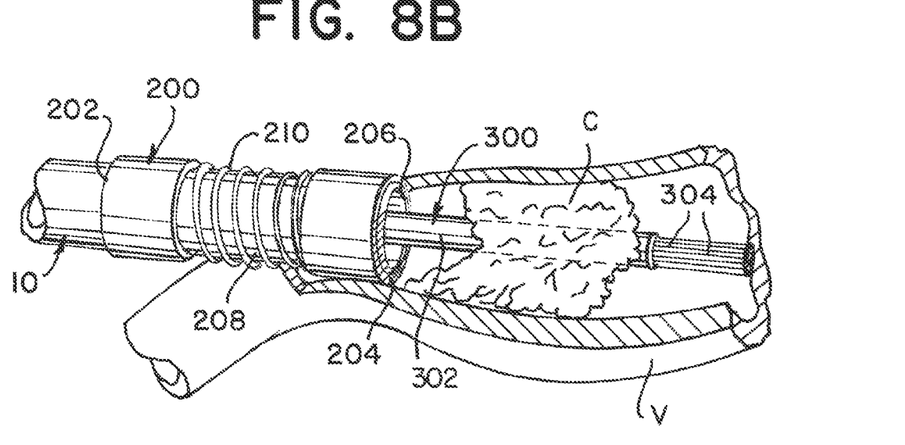
FIG. 8B illustrates the deployment of the obstruction capture device.

FIGS. 6 and 7 illustrate an example of a device 300 to remove a clot/obstruction C in the vascular system V of a patient (see FIGS. 8A-8B). The device 300 includes a delivery tube 302 sized to be passed through the catheter 10 once the obstruction C has been located using at least one of the elements 100, 200 described above. Multiple capture anchors 304 are disposed in the delivery tube 302. The capture anchors 304 can be made of a shape-memory material allow them to have an advancing position and a capture position. In the advancing position the capture anchors 304 are generally straight and are approximately parallel to a center axis 306 of the delivery tube 302. This position is illustrated in FIG. 6 and allows for the device 300 to be easily moved through the catheter 10 to the treatment location. The generally straight nature of the capture anchors 304 also assists in in penetrating through the blood clot (see FIG. 8B).

When the capture anchors 304 are in the capture position, a distal end 308 of each of the plurality of capture anchors 304 expand outwards and curves 310 proximally. Said differently, the capture anchors 304 "bloom" as they expand away from the center axis 306 and the tips of the anchors 304 curve backwards toward the delivery tube 302. Alternately, the plurality of capture anchors 304 can expand circumferentially. Thus, the most distal portion of the capture anchors 304 are the curves 310, and the tips 308 of the capture anchors 304 are pointing proximally. As the capture anchors 304 curve, they expand to approximately the diameter of the blood vessel in which they are deployed. In that way, they can anchor into a majority of the clot C to remove it from the vessel. As the delivery tube 302 is drawn back into the catheter 10, the obstruction C is captured by the capture anchors 304 and within the curve 310 of each of the plurality of capture anchors 304. Alternately, the obstruction C does not need to be displaced into the catheter 10 but removed by proximally displacing both the catheter 10 and the delivery tube 302. Aspiration can occur through the catheter 10 as the blood clot is moved to reduce or eliminate any stray piece of the clot from breaking free and passing through the blood stream. In one embodiment, the capture anchors 304 can be made of a resilient material such as spring-temper stainless steel or, more preferably a super elastic material such as Nitinol.

Figure 8C:
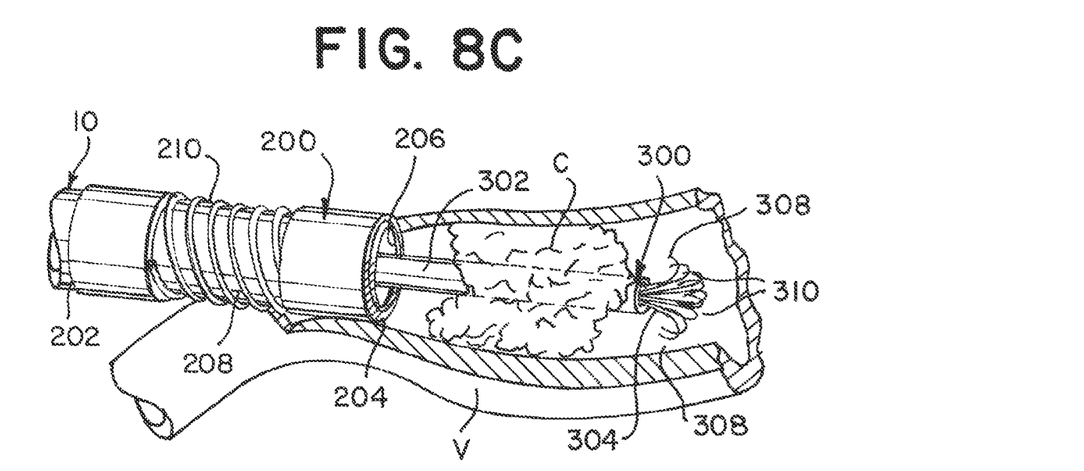
FIG. 8C illustrates the obstruction capture device deployed.

FIGS. 8A-8C illustrate an example of a clot C removal. The catheter 10 is advanced through multiple blood vessels, while a 3D image is created (Fast Anatomical Mapping) using the electromagnetic sensing element 200. The catheter 10 is advanced until resistance is sensed at the tip of the catheter 10 by the force sensor 100. This is typically an indication that the clot C has been located. See, FIG. 8A. Next, the blood clot retrieving device 300 is deployed, with the capture anchors 304 in their straight advancing position until the clot has been fully breached. See, FIG. 8B. The capture anchors 304 are advanced further into their capture position resulting in multiple nitinol preformed shapes expanding toward the wall of the blood vessel V in a circumferential way. Finally, the clot C can be pulled into the catheter lumen 16 and the entire system is removed.

Figure 9:
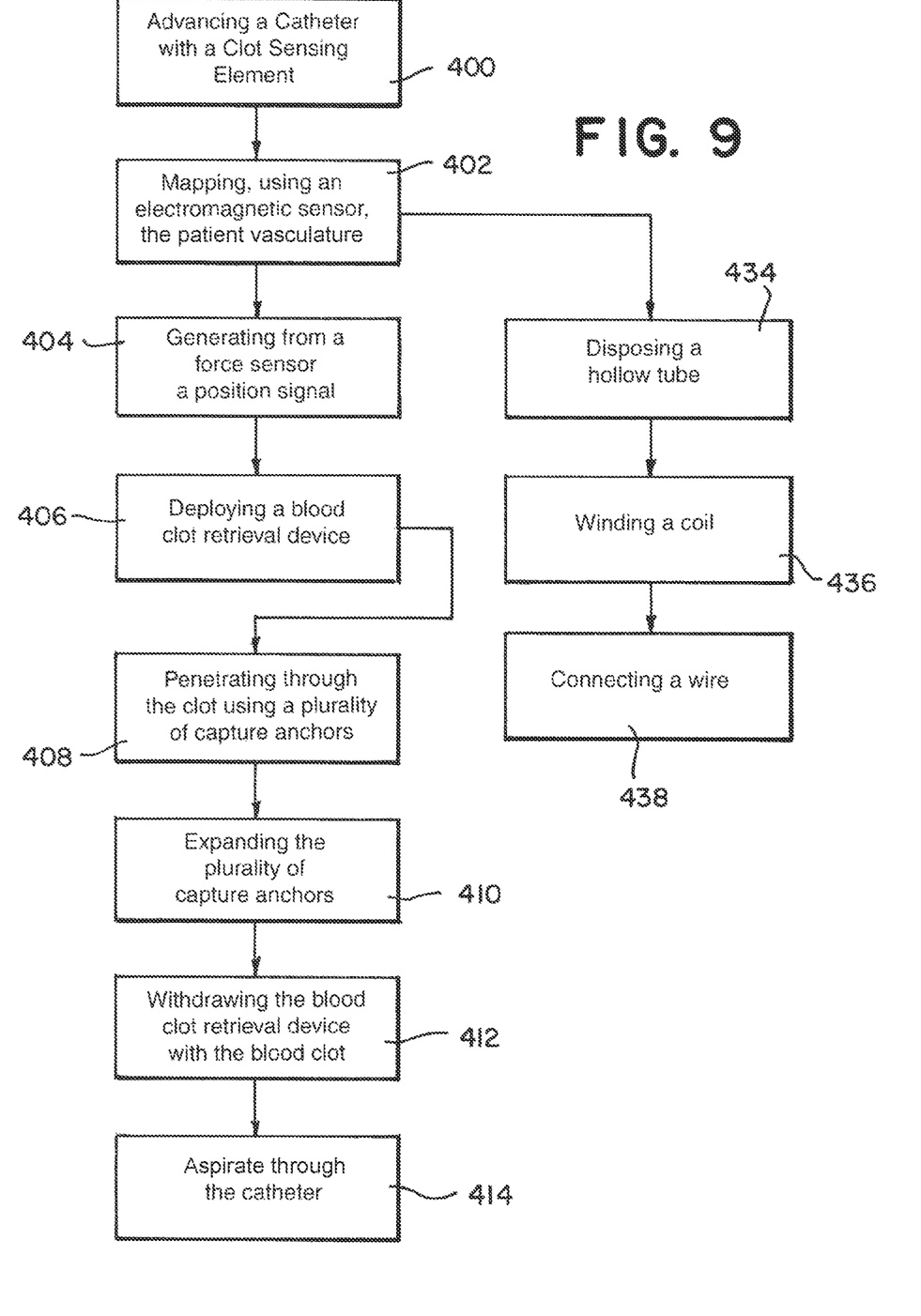
FIG. 9 is a flow chart of an example of a method of the present invention.
Figure 10:
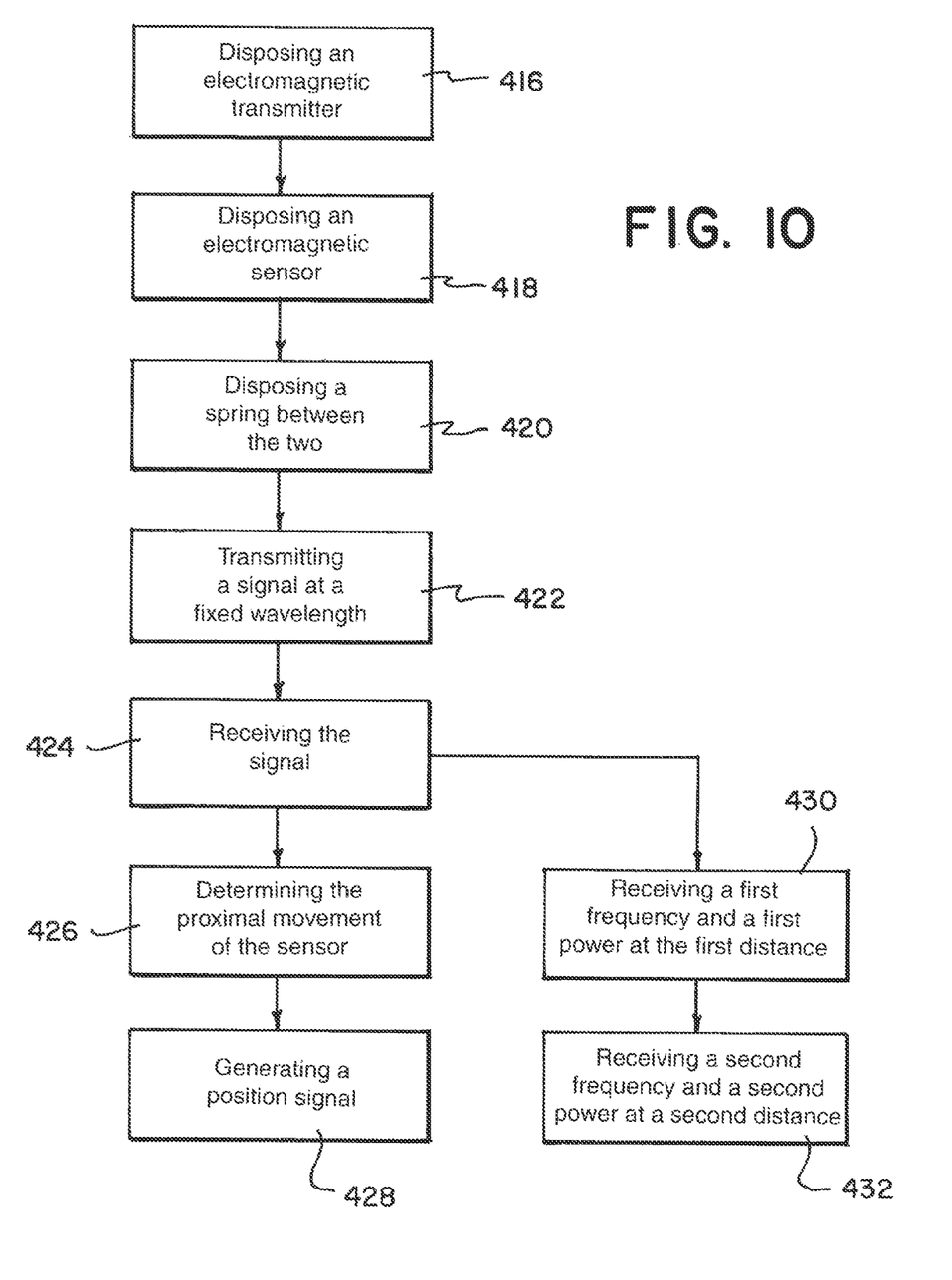
FIG. 10 is another flow chart of an example of a method of the present invention.

FIGS. 9 and 10 illustrate a method of detecting and retrieving a blood clot, having the steps of advancing a catheter 10 with a clot sensing element 100, 200 through a patient's vascular system V (step 400). Using an electromagnetic sensor 200 disposed at a distal end of the clot sensing element, the patient's vascular system V can be mapped in real-time using FAM (step 402). Once the tip of the catheter 10 contacts the clot the force sensor 100 generates a position signal indicating the clot sensing element 100, 200 contacted the clot C in the patient's vascular system V (step 404). A blood clot retrieval device 300 can be deployed through the catheter 10 and lumen 16, 206 to remove the clot C from the patient's vascular system V (step 406).

The deploying step (step 406) can also include penetrating through the clot C using the plurality of capture anchors 304 in an advancing position (step 408). The plurality of capture anchors 304 can be expanded into a capture position (step 410) and the blood clot retrieval device 300 is withdrawn back into the catheter 10 with at least a portion of the blood clot C (step 412). The withdrawing step (412) can also include aspirating through the catheter 10 (step 414).

The generating step (step 404) can have the step of disposing an electromagnetic transceiver 108 at a proximal end 102 of the clot sensing element 100, 200 (step 416) and an electromagnetic sensor 110 at a first distance GL from the electromagnetic transceiver 108 (step 418). A spring 112 can be disposed between the electromagnetic transceiver 108 and the sensor electromagnetic 110, the spring 112 providing resistance to a proximal movement of the electromagnetic sensor 110 (step 420). The electromagnetic transceiver 108 can emit a signal (step 422) which can be received at the electromagnetic sensor 110 (step 424). In an example, a processor can determine the proximal movement of the electromagnetic sensor 110 based on at least one of a change in frequency of the signal and a change in power of the signal (step 426). This can generate a position signal based on the proximal movement of the clot sensor 100 (step 428). The emitted signal, in an example, can be at a fixed wavelength/frequency.

The receiving step (step 424) can include receiving at the electromagnetic sensor 110 the signal comprising a first frequency and a first power when the electromagnetic sensor 110 is at the first distance GL (step 430). Then, receiving at the electromagnetic sensor 110 the signal comprising a second frequency and a second power when the electromagnetic sensor 110 is at a second distance GL1 shorter than the first distance GL (step 432). The change from the first frequency to the second frequency can be based on the change from the first distance GL to the second distance GL1. Further, the change from the first power to the second power can also be based on the change from the first distance to the second distance.

The mapping step (step 402) can include disposing a hollow tube 208 having proximal and distal ends 202, 204, and an inner lumen 206 (step 434). Then winding a coil 210 around the tube 208, disposed outside the inner lumen 206, to providing a mapping signal (step 436) and connecting a wire 212 to the coil 210 to transmit the mapping signal to a processor 214 (step 438). The inner lumen 206 can have an inner diameter ID configured to pass a neurovascular device, such as embolic coils, flow diverters and stents.

As noted above, the hollow tube 208 can have a hollow rigid ferrite tube approximately a length L of the electromagnetic sensing element 200 and the wire 212 can be a twisted pair.

Note that the examples above contemplate one or more elements being radiopaque and visible under fluoroscopy. The elements can be used as markers as the Catheter 10 is advanced and retreated out of the patient.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The invention claimed is:

1. A force sensing element comprising:
a center lumen;
a catheter comprising an inner lumen, a distal end, and the force sensing element disposed at the distal end;
an electromagnetic transceiver configured for at least one of emitting or receiving a signal, the electromagnetic transceiver being fixed to a proximal end of the force sensing element;
an electromagnetic sensor configured for receiving the signal, the electromagnetic transceiver being disposed at the distal end of the force sensing element, slidable along the force sensing element, and configured for generating a position signal; and
a spring disposed between the electromagnetic transceiver and the electromagnetic sensor, the spring providing resistance to a proximal movement of the electromagnetic sensor,
wherein when the electromagnetic sensor is in a first position, the signal received by the electromagnetic sensor comprises a first frequency and a first power;
wherein when the electromagnetic sensor is in a second position, the signal received by the electromagnetic sensor comprises a second frequency and a second power;
wherein the position signal is generated based on at least one of the first frequency, the second frequency, the first power, and the second power,
wherein the force sensing element is configured to detect a clot in a vascular system.

2. The force sensing element of claim 1, wherein the force sensing element is configured for use with an electromagnetic sensing element, the electromagnetic sensing element comprising:
a hollow tube comprising a proximal end, and distal end, and an inner lumen having an inner diameter configured to pass a neurovascular device;
a coil wound around the tube, disposed outside the inner lumen, and providing a mapping signal; and
a wire connected to the coil and transmitting the mapping signal to a processor, and
wherein the electromagnetic sensing element is configured to map the vascular system.

3. The force sensing element of claim 1, wherein the electromagnetic sensor further comprises a fast anatomical mapping (FAM) sensor.

4. The force sensing element of claim 1,
wherein the first position is a fully distal position on the force sensing element, and
wherein the second position is a proximal position near the electromagnetic transceiver.

5. The force sensing element of claim 1, wherein the spring further comprises a spring constant controlling an amount of force needed to move the electromagnetic sensor.

6. The force sensing element of claim 5, wherein the clot is captured within the curve of one or more of the plurality of capture anchors.

7. The force sensing element of claim 5, wherein the plurality of capture anchors expand circumferentially.

8. The force sensing element of claim 1, further comprising a plurality of capture anchors disposed in the catheter comprising an advancing position and a capture position;

wherein when the plurality of capture anchors are in the advancing position they are approximately parallel to a center axis of the catheter, and wherein when the plurality of capture anchors are in the capture position, a distal end of each of the plurality of capture anchors expand outwards and curve proximally.

9. An electromagnetic sensing element with a center lumen, comprising:

a hollow tube comprising a proximal end, and distal end, and an inner lumen;

a coil wound around the hollow tube, disposed outside the inner lumen, and providing a mapping signal; and a wire connected to the coil and transmitting the mapping signal to a processor, wherein the center lumen has an inner diameter configured to pass a neurovascular device, wherein the electromagnetic sensing element is configured to map the vascular system, wherein the electromagnetic sensing element is configured for use with a force sensing element, the force sensing element comprising:

an electromagnetic transceiver configured for at least one of emitting or receiving a signal, the electromagnetic transceiver being fixed to a proximal end of the force sensing element;

an electromagnetic sensor configured for receiving the signal, the electromagnetic transceiver being disposed at the distal end of the force sensing element, slidable along the force sensing element, and configured for generating a position signal; and a spring disposed between the electromagnetic transceiver and the electromagnetic sensor, the spring providing resistance to a proximal movement of the electromagnetic sensor, wherein when the electromagnetic sensor is in a first position, the signal received by the electromagnetic sensor comprises a first frequency and a first power;

wherein when the electromagnetic sensor is in a second position, the signal received by the electromagnetic sensor comprises a second frequency and a second power;

wherein the position signal is generated based on at least one of the first frequency, the second frequency, the first power, and the second power, and wherein the force sensing element is configured to detect a clot in a vascular system.

10. The electromagnetic sensing element of claim 9, wherein:

the tube comprises a hollow rigid ferrite tube approximately a length of the electromagnetic sensing element; and the wire is a twisted pair.

11. The electromagnetic sensing element of claim 9 further comprising a plurality of capture anchors disposed in the delivery tube comprising an advancing position and a capture position;

wherein when the plurality of capture anchors are in the advancing position they are approximately parallel to a center axis of a delivery tube, and wherein when the plurality of capture anchors are in the capture position, a distal end of each of the plurality of capture anchors expand outwards and curve proximally.

12. The electromagnetic sensing element of claim 11, wherein the clot is captured within the curve of each of the plurality of capture anchors.

13. The electromagnetic sensing element of claim 11, wherein the plurality of capture anchors expand circumferentially.

* * * * *